(12) United States Patent
Russo et al.

(10) Patent No.: US 8,840,923 B2
(45) Date of Patent: Sep. 23, 2014

(54) SLOW-RELEASE PHARMACEUTICAL FORMULATION AND PROCESS FOR ITS PREPARATION

(75) Inventors: Vincenzo Russo, Rome (IT); Elisa Liberati, Rome (IT); Nicola Cazzolla, Albano Laziale (IT); Leonardo Marchitto, Porto Recanati (IT); Lorella Ragni, Chiaravalle (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 240 days.

(21) Appl. No.: 12/745,816

(22) PCT Filed: Dec. 23, 2008

(86) PCT No.: PCT/EP2008/068256
§ 371 (c)(1),
(2), (4) Date: Jun. 2, 2010

(87) PCT Pub. No.: WO2009/083561
PCT Pub. Date: Jul. 9, 2009

(65) Prior Publication Data
US 2010/0255083 A1    Oct. 7, 2010

(30) Foreign Application Priority Data
Dec. 28, 2007   (EP) .................... 07425828

(51) Int. Cl.
*A61K 9/00*      (2006.01)
*A61K 9/16*      (2006.01)
*A61K 31/00*     (2006.01)
*A61K 9/10*      (2006.01)
*A61K 9/20*      (2006.01)
*A61K 9/14*      (2006.01)
*A61K 9/28*      (2006.01)
*A61K 31/715*    (2006.01)

(52) U.S. Cl.
CPC ............ *A61K 9/2009* (2013.01); *A61K 9/2059* (2013.01); *A61K 9/1652* (2013.01); *A61K 9/205* (2013.01); *A61K 31/00* (2013.01); *A61K 9/1611* (2013.01)
USPC ........... 424/457; 424/451; 424/422; 424/455; 424/458; 424/463; 424/464; 424/465; 424/468; 424/469; 424/474; 424/489; 424/490; 514/211.05; 514/211.08; 514/211.09; 514/252.13; 514/255.03; 514/277; 514/301; 514/396; 514/408; 514/423; 514/424; 514/428; 514/461; 514/465; 514/511; 514/613; 514/646; 514/648; 514/650; 514/651; 514/653; 514/654

(58) Field of Classification Search
CPC ......... A61K 9/00; A61K 9/0002; A61K 9/14; A61K 9/20; A61K 9/2004; A61K 9/205; A61K 9/28; A61K 9/48; A61K 31/7106; A61K 31/715
USPC ......... 424/457, 451, 452, 455, 458, 463, 464, 424/465, 468, 469, 474, 489, 490, 618; 514/211.05, 211.08, 211.09, 252.13, 514/255.03, 255.05, 277, 301, 396, 408, 514/423, 424, 428, 461, 465, 511, 613, 646, 514/648, 650, 651, 653, 654; 540/61, 63, 540/65, 66, 69, 70
See application file for complete search history.

(56) References Cited

U.S. PATENT DOCUMENTS

| | | | |
|---|---|---|---|
| 3,640,741 A | 2/1972 | Etes | |
| 4,842,866 A | 6/1989 | Horder et al. | |
| 5,456,921 A | 10/1995 | Mateescu et al. | |
| 5,597,913 A * | 1/1997 | Nicoletti et al. | 536/123.1 |
| 5,705,190 A | 1/1998 | Broad et al. | |
| 6,607,748 B1 | 8/2003 | Lenaerts et al. | |
| 7,056,957 B2 * | 6/2006 | Omidian et al. | 521/99 |
| 2002/0103181 A1 * | 8/2002 | Sen et al. | 514/200 |
| 2006/0067917 A1 | 3/2006 | Sambanis et al. | |
| 2007/0099820 A1 | 5/2007 | Lancaster et al. | |
| 2007/0110811 A1 | 5/2007 | Lancaster et al. | |

FOREIGN PATENT DOCUMENTS

| | | | | |
|---|---|---|---|---|
| EP | 0 654 048 | | 5/1995 | |
| GB | 1 355 985 | | 6/1974 | |
| GB | 1355985 | * | 6/1974 | ............... A61K 9/00 |
| JP | 62 178505 | | 8/1987 | |
| JP | 63 290809 | | 11/1988 | |
| WO | 97 22335 | | 6/1997 | |
| WO | WO97/22335 | * | 6/1997 | ............... A61K 9/20 |
| WO | 98 35992 | | 8/1998 | |
| WO | 99 47120 | | 9/1999 | |
| WO | 02 41876 | | 5/2002 | |
| WO | 2007 047922 | | 4/2007 | |

OTHER PUBLICATIONS

"Slow-release", Merriam-Webster Dictionary [online], [Retrieved Apr. 7, 2012], Retrieved from the Internet: <URL: http://www.merriam-webster.com/medical/slow-release>.*

"Sustained-release", Merriam-Webster Dictionary [online], [Retrieved Apr. 7, 2012], Retrieved from the Internet: <URL: http://www.merriam-webster.com/medical/sustained-release>.*

"Controlled-release", Dictionary.com [online], [Retrieved Apr. 7, 2012], Retrieved from the Internet: <URL: http://dictionary.reference.com/browse/controlled-release>.*

MacMillan Encyclopedia of Physics, 1996, Simon & Shuster, London; vol. 4, p. 1677.*

Nokhodchi, Ali et al., In situ cross-linking of sodium alginate with calcium and aluminum ions to sustain the release of theophylline from polymeric matrices, Il Farmaco, vol. 59, pp. 999-1004, (2004).

Snell Dee Foster et al., "Colorimetric Methods of Analysis", vol. III, p. 204, (1954).

* cited by examiner

*Primary Examiner* — Jane C Oswecki

(74) *Attorney, Agent, or Firm* — Oblon, Spivak, McClelland, Maier & Neustadt, L.L.P.

(57) ABSTRACT

Slow-release excipients which comprise an association of at least one glycogen and at least one alginate with an alkaline-earth metal salt are useful for the preparation of slow-release pharmaceutical formulations.

37 Claims, 6 Drawing Sheets

SLOW-RELEASE PHARMACEUTICAL FORMULATION AND PROCESS FOR ITS PREPARATION

CROSS REFERENCES TO RELATED APPLICATIONS

This application is a 371 of International Patent Application No. PCT/EP2008/068256, filed on Dec. 23, 2008, and claims priority to European Patent Application No. 07425828.6, filed on Dec. 28, 2007.

FIELD OF THE INVENTION

The present invention relates to a controlled-release pharmaceutical formulation and the process for the preparation thereof.

In particular, the invention relates to a controlled-release pharmaceutical formulation comprising at least one active ingredient dispersed in a matrix comprising at least one slow-release excipient comprising an association of at least one glycogen and at least one alginate with alkaline-earth metal salts, and the process for the preparation thereof.

More particularly, the invention also relates to a slow-release excipient comprising an association of at least one glycogen and at least one alginate with alkaline-earth metal salts, and the process for the preparation thereof.

STATE OF THE ART

In addition to the active ingredient, pharmaceutical compositions for the administration of drugs include auxiliary substances known as excipients.

Excipients have various important roles to play in the processes of the manufacture, preservation and use of pharmaceutical formulations.

Depending upon their role, excipients are classified as filler excipients, production excipients, preservative excipients, presentation excipients and release excipients.

Excipients having a role as a filler comprise diluents, which are used to increase the volume of a pharmaceutical formulation, absorbents, which are used to absorb and retain moisture, and adsorbents, which are used to adsorb gases, toxins and bacteria.

Excipients having a production role are lubricants, used in the preparation of tablets, which prevent powders from adhering to both the dies and punches of the tabletting machine, binders, which impart compactness to the pharmaceutical form, glidants which improve the ability of powders to run, plasticizers and viscosity modifiers.

Excipients having a preservative role are useful for ensuring the stability of pharmaceutical preparations in terms of chemical, physical, microbiological, toxicological and therapeutic properties. These excipients include antibiotics which prevent the growth of microorganisms, antioxidants which reduce oxidative degradation of the active ingredients, and chelating agents which complex metals capable of catalysing reactions degrading the active ingredients.

Excipients having a presentation role are used to make the pharmaceutical form more pleasant for patients, and include flavourings, sweeteners and colouring agents.

Among the excipients which have a role in release of the active ingredient there are disaggregating agents, which on contact with biological fluids encourage disaggregation of the pharmaceutical form, and polymers, used as coating substances or as matrices for achieving release of the active ingredient which changes over time.

The polymers mainly used to modify or control the release of active ingredient are for example polyesters, carbomers, cellulose acetophthalate, hydroxypropylmethyl cellulose, polymethacrylates, ethyl cellulose, polyoxyethylene and cross-linked polysaccharides.

Chemically-modified polysaccharides of plant origin such as, for example, starch or its components (amylose and amylopectin) have had great success in recent years because of their non-toxic and biodegradable properties.

U.S. Pat. No. 5,456,921 describes a slow-release pharmaceutical form comprising a mixture of active ingredient and a cross-linked polymer obtained from amyloses which has been cross-linked with epichlorohydrin or 2,3-dibromopropanol.

Patent application WO 98/35992 describes a process for the preparation of a slow-release excipient based on starch with a high amylose content, comprising a step of gelatinisation, a step of cross-linking, a step of desalting, a step of heat treatment, and finally a step of drying the slow-release excipient.

U.S. Pat. No. 6,607,748 describes a similar process to the above in which the cross-linking step is carried out before the gelatinisation step, and describes how smaller quantities of reagent are used in that way and a material having better slow-release properties is obtained.

Another example of excipients used in the preparation of slow-release oral formulations are alginic acid derivatives, and in particular their salts with alkali metals. Alginic acid is a copolymer comprising β-D-mannuronic acid and α-L-glucuronic acid linked by means of 1-4 glycoside bonds. Sodium alginate is extracted from various types of algae and the number of individual monosaccharide residues and their sequence in the chain depends on the nature of the original alga.

Patents GB 1,355,985 and U.S. Pat. No. 3,640,741 describe the preparation of mixtures of sodium alginate and calcium salts for the preparation of slow-release pharmaceutical formulations.

U.S. Pat. No. 4,842,866 describes solid slow-release pharmaceutical formulations comprising an active ingredient and a mixture of sodium alginate and sodium and calcium alginate.

Patent application WO 97/22335 describes a formulation similar to the above which also comprises the presence of an organic carboxylic acid to assist dissolution of an active ingredient of a basic nature.

Patent application US 2002/0103181 describes a controlled-release tablet comprising a betalactam antibiotic as the active ingredient and a mixture of sodium alginate and xanthan gum, which depending upon the quantity of diluents offers slower or faster release of the active ingredient.

Il Farmaco 59, 2004, 999-1004 describes the progress of the release of theophilline from a formulation comprising sodium alginate and calcium chloride or aluminium chloride in various ratios.

Glycogen is a polysaccharide of animal origin mainly comprising molecules of D-glucose bound by α-1-4 glycoside bonds with branches every 5-10 glucose units formed by α-1-6 glycoside bonds. The number and degree of branching of the glycogen vary according to the animal species from which it is obtained. The molecular weight of natural glycogen is of the order of $10^6$-$10^7$ Dalton. In nature glycogen is always bound to a protein, glycogenin, an enzyme correlated with the cellular process of glycogen synthesis. The quality of a commercial glycogen depends on the presence of greater or lesser quantities of protein residues (measured in terms of quantity of nitrogen expressed as ppm) and reducing sugars.

Patent EP 654,048 describes a high quality glycogen with a low nitrogen and reducing sugars content.

Glycogen is used as an emollient (as described in JP-A-87-178 505) and a hydrating agent (as described in JP-A-88-290 809) in the cosmetics industry, as an additive in the food industry, and as a humectant and lubricant in ophthalmic solutions (as described in patent WO 99/47120).

The Applicant has noted that the slow-release formulations known in the art have many disadvantages.

The first disadvantage lies in the poor stability and reproducibility of compositions comprising mixtures of sodium alginate and calcium salts, probably because of the high reactivity of the alginate to calcium ions.

A second disadvantage comprises a relatively short release profile, which does not make it possible to prepare single daily dose pharmaceutical formulations (that is, for administration once a day) or even multi-day doses (i.e. for administration once every two, three or more days).

The third disadvantage comprises the fact that the release profile often differs from the ideal zero kinetics profile (i.e. release at a constant rate), the release rate being initially very high and then reducing, or a release rate which is initially very low and then increases, or a rate which is variable and unforeseeable.

DEFINITIONS

For the purposes of this description and the following claims the term "association" is intended to mean a mixture of constituents among which bonds of an ionic, electrostatic, hydrophilic, lipophilic, polar, or covalent nature are formed individually or in any combination.

SUMMARY OF THE INVENTION

Surprisingly, the Applicant has found that the association of at least one glycogen and at least one alginate with alkaline-earth metal salts obtained through the formation of a hydrogel, and subsequent drying thereof, makes it possible to produce slow-release pharmaceutical formulations comprising an active ingredient and the said association as a release excipient which overcome the above-mentioned disadvantages.

Therefore, the present relates to a pharmaceutical formulation comprising at least one active ingredient dispersed in a matrix comprising at least one slow-release excipient comprising an association of at least one glycogen and at least one alginate with alkaline-earth metal salts.

The Applicant has found that the pharmaceutical formulation according to the present invention is stable over time and easily reproducible, and has none of the typical disadvantages of formulations incorporating calcium alginate.

The Applicant has also observed that the pharmaceutical formulation according to the present invention is able to release the active ingredient with release kinetics which are substantially of zero order, that is to say constant over time.

Furthermore, the Applicant has observed that release of the active ingredient takes place over a period of twelve or more hours, thus making single daily dose or multiple-day dose administration possible (depending upon the bioavailability of the active ingredient).

In another aspect, the present invention also relates to a slow-release excipient for the preparation of pharmaceutical formulations comprising an association of at least one glycogen and at least one alginate with alkaline-earth metal salts.

In a further aspect, the present invention relates to a process for the production of a slow-release excipient comprising an association of at least one glycogen and at least one alginate with alkaline-earth metal salts which comprises the steps of:
(a) dissolving the said at least one glycogen and the said at least one alginate in a hydrophilic medium,
(b) adding a salt of an alkaline-earth metal which is soluble in the said hydrophilic medium,
(c) stirring the said hydrophilic medium and allowing it to stand until the hydrophilic medium gels with the formation of a hydrogel, and
(d) dehydrating the said hydrogel.

The Applicant has observed that the process of production according to the present invention is economically advantageous, is readily suitable for industrial application, has high reproducibility and produces a slow-release excipient which makes it possible to produce pharmaceutical forms having improved slow-release properties.

DETAILED DESCRIPTION OF THE INVENTION

Figure 1:
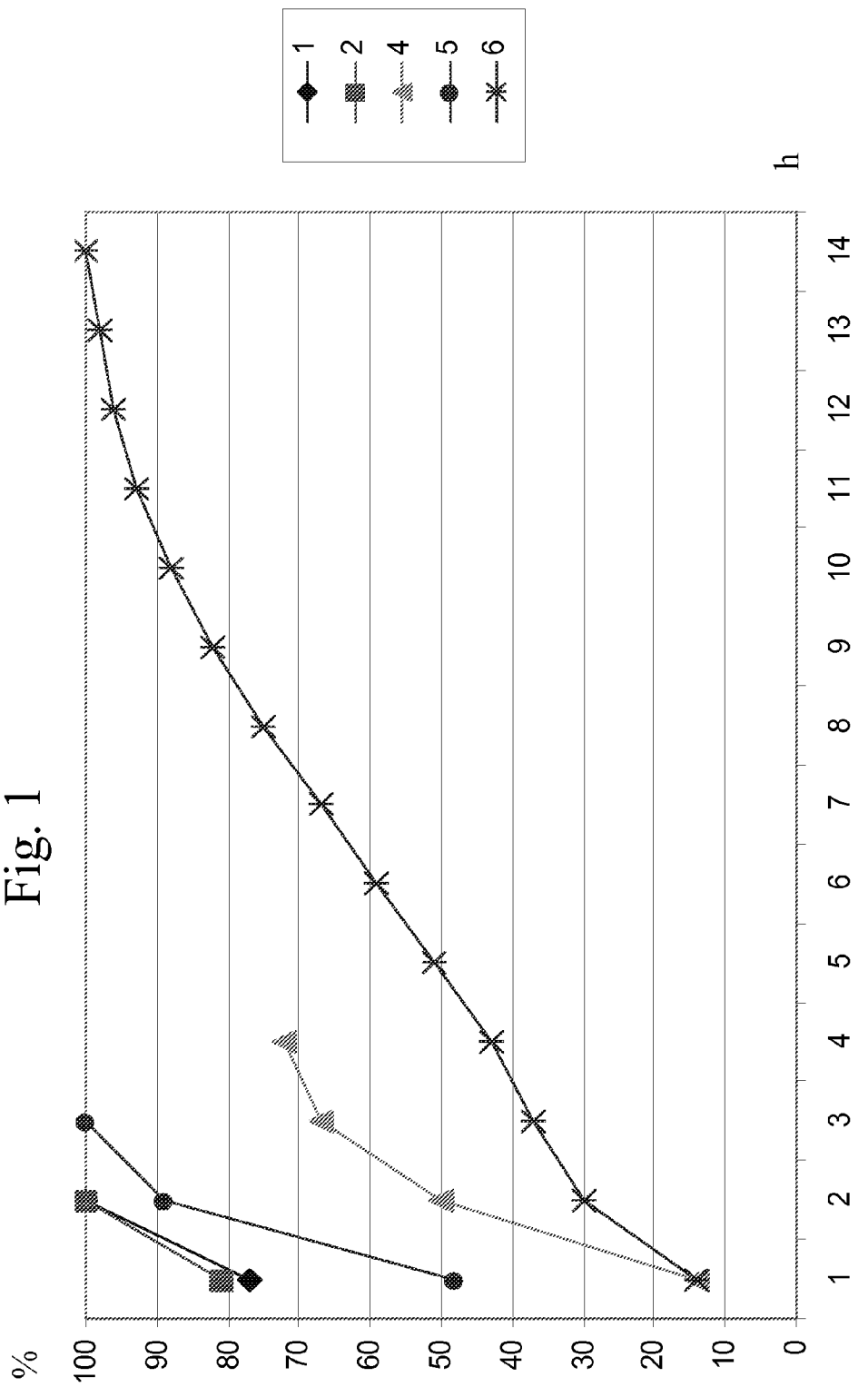
FIG. 1 shows the release profile for tablets 1, 2 and 4 to 6 in Example 2.

The present invention therefore relates to a pharmaceutical formulation comprising at least one active ingredient dispersed in a matrix comprising at least one slow-release excipient comprising an association of at least one glycogen and at least one alginate with alkaline-earth metal salts.

In addition to this, the present invention also relates to a slow-release excipient for the preparation of pharmaceutical formulations comprising an association of at least one glycogen and at least one alginate with alkaline-earth metal salts.

The glycogen used in the present invention is obtained from natural glycogen which can be extracted from animals or fungi. Molluscs, in particular mussels (*Mytilus edulis* and *Mytilus gallus provincialis*) are a particularly useful source of glycogen because they are available in large quantities at low cost and contain a reasonable amount of glycogen (on average between 2.5% and 3.9% by weight). Other natural sources of glycogen include other bivalve molluscs such as clams, oysters, some species of gastropods or sea snails, such as limpets (*Crepidula formicata*, the slipper limpet), as well as the organs of vertebrate animals which are rich in glycogen such as the liver and muscles.

The glycogen used in the present invention may be used as obtained from extraction processes or may be treated in subsequent purification processes. As already mentioned previously, the quality of a commercial glycogen will depend on the presence of a greater or lesser quantity of protein residues (measured in terms of quantity of nitrogen, expressed as ppm) and reducing sugars.

For the purposes of the present invention it is preferred to use a glycogen having a low reducing sugars and nitrogen content. Examples of commercial products preferably used in the present invention are glycogens produced and distributed by Sigma-Aldrich.

Preferably the glycogen used in the present invention comprises less than 1% by weight, and more preferably less than 0.25% by weight of reducing sugars measured according to the method of F. D. Snell and Snell, "Colorimetric methods of analysis", New York, 1954, vol. III, p. 204.

Preferably the glycogen used in the present invention comprises less than 3,000 ppm of nitrogen, more preferably less than 1,000, and even more preferably less than 100 ppm of nitrogen, measured by the Kjeldahl method.

Preferably, the glycogen used in the present invention is Polglumyt™ glycogen, the trade name of a deproteinated glycogen produced and distributed by A.C.R.A.F. S.p.A., Rome, Italy, and obtained using the purification process described in patent EP 654048B1.

The alginate used in the present invention is obtained by extraction from marine algae.

The marine algae most frequently used belong to the species *Ascophyllum, Durvillaea, Ecklonia, Laminaria, Lessonia, Macrocystis* and *Sargassum*.

Choice of the type of alga is based on economic considerations associated with its alginate content and its ability to gel. Preferred algae are those which contain a greater content of readily extractable alginate with better gelling properties.

Alginate is extracted by dispersing the chopped algae in a hot alkaline solution, generally sodium carbonate. Within two hours the alginate present in the algae dissolves in the form of sodium alginate and the solution becomes a pulp which also contains the insoluble parts of the algae, mainly cellulose. After dilution in order to reduce its viscosity the pulp is pre-filtered using diatomaceous earth and then filtered in a filter press. The resulting solution is then acidified to release the alginic acid, dried, and the alginic acid is then again dissolved in the solution of sodium carbonate and again dried, with the formation of sodium alginate.

The alginate mainly used in implementing the present invention is sodium alginate, but any other type of alginate salt may be used provided that it is soluble in an aqueous medium, such as for example potassium alginate or ammonium alginate.

As mentioned previously, alginic acid is a copolymer comprising units of β-D-mannuronic acid and α-L-glucuronic acid. As a consequence, sodium alginate comprises sodium β-D-mannuronate and sodium α-L-glucuronate units. The sodium alginate preferably used in the present invention has a molecular weight of between 10,000 and 600,000 Dalton. The sodium alginate used in the present invention may be characterised by the viscosity of its 1% by weight aqueous solution. The viscosity may vary within the range from 50 to 1500 cPs, within which a distinction may be made between low-viscosity alginates in the range from 50 to 200 cPs, medium viscosity alginates in the range from 200 to 500 cPs, and high viscosity alginates in the range from 500 to 1500 cPs.

Low/medium viscosity alginates are preferred for the purposes of the present invention. Examples of commercial alginates which are preferably used in the present invention are Keltone®, Manucol®, Manugel®, Kelcosol®, Kelset® (marketed by ISP Pharmaceuticals), Protanal® (marketed by FMC BioPolymer), Sigma® A2158 and A2033 (marketed by Sigma-Aldrich).

In preparation of the association according to the present invention the ratio by weight between the glycogen and the alginate (calculated as sodium alginate) is preferably between 90:10 and 10:90, more preferably between 90:10 and 30:70, and even more preferably between 85:15 and 50:50.

The alkaline-earth metal salts used in the present invention are selected from the group of the water-soluble salts of magnesium, calcium, strontium and barium. The choice of salt is not particularly restricting. Useful examples are halides, sulphates, sulphites, carbonates, bicarbonates, phosphates and so on. Specific examples of alkaline-earth metal salts are magnesium chloride, calcium chloride, strontium chloride, barium chloride, magnesium bromide, calcium bromide, barium bromide, strontium bromide, barium iodide, calcium iodide, strontium iodide, magnesium sulphate, magnesium carbonate, calcium bicarbonate, magnesium bicarbonate, barium bicarbonate, or calcium dihydrogen phosphate. The salts preferably used in the present invention are calcium chloride, calcium bromide, barium chloride, barium bromide, strontium chloride and strontium bromide.

The quantity of salts of alkaline-earth metals used in the association according to the present invention is preferably between 0.050 and 5.000 millimoles, more preferably between 0.100 and 2.000 millimoles, and even more preferably between 0.100 and 1.000 millimoles per gram of glycogen/alginate mixture.

The active ingredient used in the present invention is selected from the group of active ingredients which can be administered orally. The present invention is particularly useful with active ingredients which require controlled administration over a period of time of more than 12 hours, preferably equal to or more than 24 hours.

Useful examples of active ingredients are selected from the group comprising analgesics, antipyretics, antibiotics, antihistamines, anxiolytics, anti-inflammatories, antacids, vasodilators, vasoconstrictors, stimulants, decongestants, anticoagulants, antiarrhythmics, hypoglycaemic agents, diuretics, antidepressants, antiasthmatics, anti-emetics, and antihypotensive and antispasmodic agents.

Specific examples of the active ingredients preferably used in the present invention are ibuprofen, paracetamol, prulifloxacin, levocetirizine dihydrochloride, lorazepam, naproxen, ranitidine hydrochloride, isosorbide, naphazoline nitrate, pyracetam, ticlopidine hydrochloride, propaphenone hydrochloride, glimepiride, furosemide, trazodone hydrochloride, flunisolide and dimehydrinate.

The quantity of active ingredient used in manufacture of the pharmaceutical form according to the present invention is preferably between 5% by weight and 60% weight relative to the total weight of the pharmaceutical form, more preferably between 10% and 50% by weight, and even more preferably between 20% and 40% by weight.

The pharmaceutical form according to the present invention may also contain other pharmaceutically acceptable excipients in addition to the slow-release excipient according to the present invention. By the term pharmaceutically acceptable excipient is meant, inclusively without any particular limitations, any material suitable for the preparation of a pharmaceutical composition which has to be administered to a living being.

Such materials, known in the art, are for example anti-adherence agents, binders, disintegrating agents, fillers, diluents, flavourings, colouring agents, fluidisers, lubricants, preservatives, humectants, absorbents and sweeteners.

Useful examples of pharmaceutically acceptable excipients are sugars, such as lactose, glucose or sucrose, starches, such as corn starch and potato starch, cellulose and its derivatives, such as sodium carboxymethyl cellulose, ethyl cellulose and cellulose acetate, gum tragacanth, malt, gelatin, talc, cocoa butter, waxes, oils, such as peanut oil, cottonseed oil, safflower oil, sesame oil, olive oil, corn oil and soya oil, glycols such as polypropylene glycol, polyols, such as glycerine, sorbitol, mannitol and polyethylene glycol, esters, such as ethyl oleate and ethyl laurate, agar agar, and so on.

The pharmaceutical form according to the present invention may be any composition which is useful for the controlled oral administration of an active ingredient such as for example suspensions, emulsions, powders, tablets, granulates, pellets, capsules, lozenges and pills.

Preferably the pharmaceutical form according to the present invention comprises an enteric coating which is resistant to the gastric environment and which promotes onset of release of the active ingredient in the intestinal tract.

According to a further aspect the present invention relates to a process for producing a slow-release excipient comprising an association of at least one glycogen and at least one alginate with salts of alkaline-earth metals which comprises the steps of:
(a) dissolving the said at least one glycogen and the said at least one alginate in a hydrophilic medium,
(b) adding a salt of an alkaline-earth metal which is soluble in the said hydrophilic medium,
(c) stirring the said hydrophilic medium and allowing it to stand until the hydrophilic medium gels with the formation of a hydrogel, and
(d) dehydrating the said hydrogel.

The total quantity of glycogen and alginate (calculated as sodium alginate) added to the hydrogel preparation is preferably between 1% by weight and 20% by weight relative to the volume of the hydrophilic medium, which preferably comprises distilled water, used to dissolve them. More preferably the quantity lies between 1% and 15% (w/v), and even more preferably between 1% and 10% (w/v).

The preferred hydrophilic medium is distilled water, demineralised water or deionised water, which is preferably sterilised, for example by exposure to ultraviolet rays.

Dissolution is preferably carried out with stirring, by means of a mechanical or magnetic stirrer, depending upon the scale of the production process.

Dissolution step (a) is conveniently carried out at room temperature. The temperature of the hydrophilic medium, preferably purified or distilled water, may be higher than room temperature in order to further favour the rate of dissolution. Preferably the temperature is in any event less than 50° C.

Step (b) of adding the salt of an alkaline-earth metal comprises the addition of the salt in the solid phase or, preferably, in aqueous solution. The concentration of the alkaline-earth salt in the solution added is preferably between 0.01 N and 1 N, preferably between 0.05 and 0.5 N. The quantity of alkaline-earth salt added to the glycogen and alginate solution obtained in step (a) is preferably between 0.050 and 5.000 millimoles, more preferably between 0.100 and 2.000 millimoles, and even more preferably between 0.100 and 1.000 millimoles per gram of glycogen/alginate mixture.

The alkaline-earth salt is added with stirring. After addition, stirring is maintained for a period of time in step (c). The stirring time may vary, but it is preferably between 10 and 120 minutes, or preferably between 30 and 60 minutes. After stirring, step (c) ends with a resting time, preferably of between 6 and 24 hours, more preferably between 8 and 16 hours. During this step the alkaline-earth metal ions, preferably selected from calcium, barium and strontium, promote the creation of an association between glycogen, alginate and the metal ions themselves with the formation of bonds of various kinds (which may be covalent, ionic, electrostatic, hydrophilic, lipophilic or polar), individually or in any combination, and a sol-gel transition with the formation of a hydrogel.

In the subsequent step (d) of the process according to the present invention the water present in the hydrogel obtained at the end of step (c) is removed by conventional drying and dehydrating techniques until an anhydrous powder comprising the slow-release excipient according to the present invention, comprising in a preferred aspect the association of a glycogen and an alginate with salts of calcium, barium or strontium, is obtained.

The present invention also includes the process of producing a pharmaceutical form comprising at least one active ingredient dispersed in the matrix comprising at least one slow-release excipient comprising an association of at least one glycogen and at least one alginate with alkaline-earth metal salts, as described previously.

The present invention therefore comprises a process for the production of a pharmaceutical form comprising at least one active ingredient dispersed in a matrix comprising at least one slow-release excipient which comprises the steps of
A. preparing an association of at least one glycogen and at least one alginate with alkaline-earth metal salts,
B. mixing the said active ingredient with the said association,
C. optionally, adding at least one further pharmacologically acceptable excipient, and
D. producing the pharmaceutical form selected from the group comprising suspensions, emulsions, powders, tablets, granulates, pellets, capsules, lozenges and pills.

Preparation of the association according to step (A) is preferably carried out as described above. Step (B) of mixing the active ingredient is preferably carried out after formation of the association until a homogeneous dispersion is obtained.

However step (B) of mixing the active ingredient may also take place during the step (A) of preparing the association. In this case the active ingredient may be added before, during or after any of steps (a), (b), and (c) described previously in the process of producing the association of at least one glycogen and at least one alginate with alkaline-earth metal salts.

In particular the active ingredient may be added during first step (a), before, together with or after the addition of glycogen and alginate, in step (b) before, together with or after addition of the salt of an alkaline-earth metal, or in step (c) during stirring, after stirring, before or after formation of the hydrogel. Preferably, the active ingredient may be added in step (a).

During the optional step (C) at least one further pharmacologically acceptable excipient is added. As described previously, these materials are known in the art and comprise, for example, anti-adherence agents, binders, disintegrating agents, fillers, diluents, flavourings, colouring agents, fluidisers, lubricants, preservatives, humectants, absorbents and sweeteners.

The final pharmaceutical form is produced in step (D) using conventional techniques for obtaining suspensions, emulsions, powders, tablets, granulates, pellets, capsules, lozenges and pills which may comprise the steps of granulation, dissolution, drying, mixing, grinding, sieving, sterilisation, compression, and so on. Preferably the pharmaceutical form according to the present invention is subjected to a final treatment of coating with a layer of enteric coating which is resistant to the gastric environment.

The following examples serve to illustrate the invention without however restricting it.

Example 1

Description of the Procedures

The procedures used in preparation of the tablets are described below.

Procedure A (Comparison)

A solution in distilled water containing the percentage in W/V of polymer ingredients indicated in Tables 1-4 below in the ratio indicated in Tables 1-4 below was prepared in a 500 ml beaker with vigorous mechanical stirring.

The solution so obtained was dried and ground. The powder so obtained was mixed with the active ingredient in the proportions indicated in Tables 1-4 below, and granulated with distilled water in a mortar.

The granulate so obtained was dried in a stove under vacuum at a temperature of approximately 50-60° C. overnight, ground in a mortar and sieved to the desired particle size (0.125 mm).

250 mg aliquots were then obtained and converted into tablets using a hydraulic press at a pressure of 2.5 tons/cm$^2$ for 3 minutes.

Procedure B (Comparison)

The polymer ingredients in the ratio indicated in Tables 1-4 below were mixed with the active ingredient in the proportions indicated in Tables 1-4 below, and then granulated with distilled water in a mortar. The granulate so obtained was dried in a stove under vacuum at a temperature of approximately 50-60° C. overnight, ground in a mortar and sieved to the desired particle size (0.125 mm).

250 mg aliquots were then taken and converted into tablets using a hydraulic press at a pressure of 2.5 tons/cm$^2$ for 3 minutes.

Procedure C (Invention)

A solution in distilled water containing the percentage in W/V of polymer ingredients indicated in Tables 1-4 below in the ratio indicated in Tables 1-4 below was prepared in a 500 ml beaker with vigorous mechanical stirring.

A 0.1 N aqueous solution of $CaCl_2$ (or $BaCl_2$ or $SrCl_2$ if otherwise indicated) was added in the quantity indicated in Tables 1-4 below, stirring for approximately 1 hour, and then allowing to stand overnight with the formation of a hydrogel.

The hydrogel obtained was dried, ground, homogeneously mixed with the active ingredient in the proportions indicated in Tables 1-4 below and then granulated with distilled water in a mortar.

The granulate so obtained was dried in a stove under vacuum at a temperature of approximately 50-60° C. overnight, ground in a mortar and sieved to the desired particle size (0.125 mm).

250 mg aliquots were then taken and then converted into tablets using a hydraulic press at a pressure of 2.5 tons/cm$^2$ for 3 minutes.

Procedure D (Comparison)

The polymer ingredients in the ratio indicated were mixed with the active ingredient in the proportions indicated in Tables 1-4 below.

250 mg aliquots were then taken and converted into tablets using a hydraulic press at a pressure of 2.5 tons/cm$^2$ for 3 minutes.

Example 2

Preparation of Tablets 1-6

A series of tablets from 1 to 6 containing the ingredients in Table 1 were prepared using the procedures indicated in Table 1. The active ingredient used was trazodone hydrochloride.

TABLE 1

|  | 1(C) | 2(C) | 3(C) | 4(C) | 5(C) | 6(I) |
|---|---|---|---|---|---|---|
| Polymer | Polglumyt | Polglymyt | Alginate | Alginate | Polglumyt/Alginate | Polglumyt/Alginate |
| Ratio | 100 | 100 | 100 | 100 | 90/10 | 90/10 |
| Procedure | A | B | B | C | B | C |
| 0.1 N $CaCl_2$ solution (ml/100 ml) | — | — | — | 15 | — | 10 |
| % polymer in solution (W/V) | 2 | — | — | 2 | — | 8 |
| % active ingredient (W/W) | 23 | 23 | 23 | 23 | 23 | 23 |

(C)Comparison
(I)Invention

Polglumyt: glycogen comprising less than 60 ppm of nitrogen and less than 0.25% by weight of reducing sugars prepared in accordance with the procedure described in EP 654,048.
Alginate: sodium alginate from brown algae, viscosity of the 2% solution at 25° C. approximately 250 cPs. Manufacturer Sigma-Aldrich. Manufacturer's code SIGMA A2158.

Tablets 1, 2, 4, 5 and 6 were subjected to dissolution tests in phosphate buffer (USP XXIII) for a period of 24 hours maintaining a pH value of 6.4 for the first hour and 7.4 for the remaining 23 hours. The granulate in preparation 3 proved to be difficult to process and it was not possible to prepare the corresponding tablet.

The results are illustrated in Table R1 below and in FIG. 1.

TABLE R1

| Time (hours) | 1(C) | 2(C) | 4(C) | 5(C) | 6(I) |
|---|---|---|---|---|---|
|  | % of drug released | | | | |
| 1 | 77 | 81 | 14 | 48 | 14 |
| 2 | 100 | 100 | 50 | 89 | 30 |
| 3 |  |  | 67 | 100 | 37 |
| 4 |  |  | 72 |  | 43 |
| 5 |  |  |  |  | 51 |
| 6 |  |  |  |  | 59 |
| 7 |  |  |  |  | 67 |
| 8 |  |  |  |  | 75 |
| 9 |  |  |  |  | 82 |
| 10 |  |  |  |  | 88 |
| 11 |  |  |  |  | 93 |
| 12 |  |  |  |  | 96 |
| 13 |  |  |  |  | 98 |
| 14 |  |  |  |  | 100 |

(C)Comparison
(I)Invention

The data in Table R1 clearly show that tablets 1, 2 and 4 comprising glycogen or alginate alone did not show slow-release properties regardless of the type of procedure used. Similarly, tablet 5 comprising a mixture of glycogen and alginate obtained using procedure B showed no slow-release properties. Conversely, tablet 6 comprising the association glycogen-calcium chloride-alginate according to the present invention showed excellent slow-release properties with kinetics of almost zero order over a period of approximately 14 hours.

Example 3

Preparation of Tablets 7-10

A series of tablets from 7 to 10 containing the ingredients in Table 2 were prepared according to the procedures indicated in Table 2. The active ingredient used was trazodone hydrochloride.

TABLE 2

|  | 7 ($^C$) | 8 ($^C$) | 9 ($^I$) | 10 ($^C$) |
|---|---|---|---|---|
| Polymer | Polglumyt/ Alginate | Polglymyt/ Alginate | Polglumyt/ Alginate | Polglumyt/ Alginate |
| Ratio | 80/20 | 80/20 | 80/20 | 80/20 |
| Procedure | A | B | C | D |
| 0.1 N CaCl$_2$ solution (ml/100 ml) | — | — | 6 | — |
| % polymer in solution (W/V) | 2 | — | 2 | — |
| % active ingredient (W/W) | 23 | 23 | 23 | 23 |

($^C$): Comparison
($^I$): Invention
Polglumyt: glycogen comprising less than 60 ppm of nitrogen and less than 0.25% by weight of reducing sugars prepared in accordance with the procedure described in EP 654,048.
Alginate: sodium alginate from brown algae, viscosity of the 2% solution at 25° C. approximately 250 cPs. Manufacturer Sigma-Aldrich. Manufacturer's code SIGMA A2158.

Tablets 7 to 10 were subjected to dissolution tests in phosphate buffer (USP XXIII) for a period of 24 hours maintaining a pH value of 6.4 for the first hour and 7.4 for the remaining 23 hours.

Figure 2:
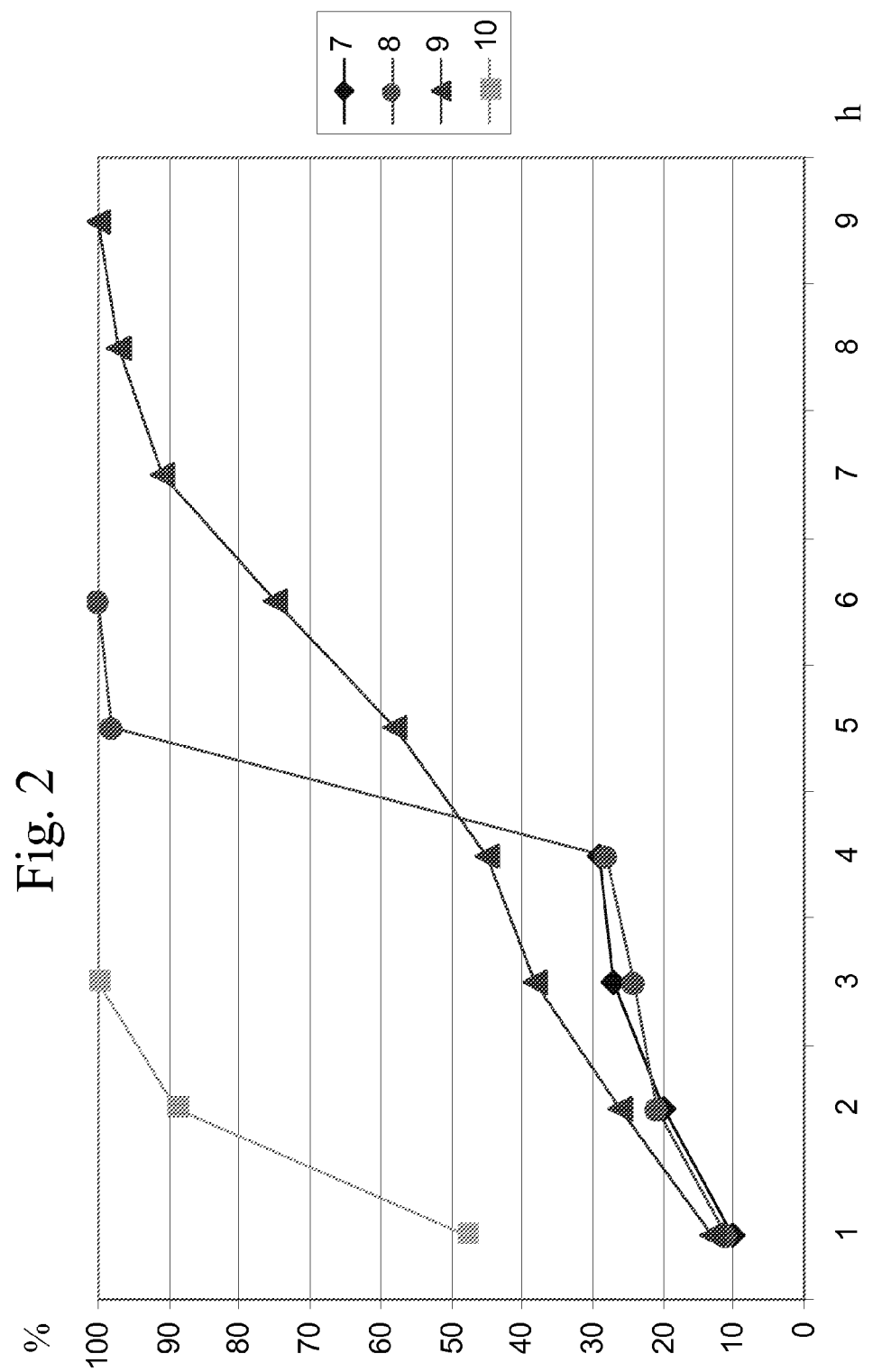
FIG. 2 shows the release profile for tablets 7 to 10 in Example 3.

The results are illustrated in Table R3 below and in FIG. 2.

TABLE R2

|  | 7 ($^C$) | 8 ($^C$) | 9 ($^I$) | 10 ($^C$) |
|---|---|---|---|---|
| Time (hours) |  | % of the drug released |  |  |
| 1 | 20 | 11 | 16 | 48 |
| 2 | 35 | 21 | 31 | 89 |
| 3 | 38 | 24 | 40 | 100 |
| 4 | 41 | 28 | 44 |  |
| 5 | 43 | 98 | 49 |  |
| 6 | 46 | 100 | 56 |  |
| 7 | 49 |  | 65 |  |
| 8 | 51 |  | 76 |  |
| 9 | 53 |  | 94 |  |
| 10 | 55 |  | 97 |  |
| 11 | 57 |  | 100 |  |
| 12 | 59 |  |  |  |
| 13 | 60 |  |  |  |
| 14 | 61 |  |  |  |

($^C$): Comparison
($^I$): Invention

The data in Table R2 clearly show that tablets 7 comprising mixtures of glycogen and alginate prepared according to procedure A do not show good release kinetics and the matrix tends to not give up all the drug present in it. In addition to this, tablets 8 and 10 comprising mixtures of glycogen and alginate prepared according to procedures B and D respectively showed no slow-release properties. Conversely, tablet 9 comprising the association glycogen-calcium chloride-alginate according to the present invention showed slow-release properties with kinetics of almost zero order over a period of approximately 11 hours.

Example 4

Preparation of Tablets 11-13

A series of tablets from 11 to 13 containing the ingredients in Table 3 were prepared according to procedure C. The active ingredient used was trazodone hydrochloride.

TABLE 3

|  | 11 ($^I$) | 12 ($^C$) | 13 ($^C$) |
|---|---|---|---|
| Polymer | Polglumyt/ Alginate | Amylopectin/ Alginate | Starch/ Alginate |
| Ratio | 80/20 | 80/20 | 80/20 |
| 0.1 N CaCl$_2$ solution (ml/100 ml) | 6 | 6 | 6 |
| % polymer in solution (W/V) | 2 | 2 | 2 |
| % active ingredient (W/W) | 23 | 23 | 23 |

($^C$): Comparison
($^I$): Invention
Polglumyt: glycogen comprising less than 60 ppm of nitrogen and less than 0.25% by weight of reducing sugars prepared in accordance with the procedure described in EP 654,048.
Alginate: sodium alginate from brown algae, viscosity of the 2% solution at 25° C. approximately 250 cPs. Manufacturer Sigma-Aldrich. Manufacturer's code SIGMA A2158.
Amylopectin: corn amylopectin, manufacturer Fluka. Manufacturer's code 10120.
Starch: wheat starch (purified). Manufacturer Sigma-Aldrich. Manufacturer's code SIGMA S-2760.

Tablets 11 to 13 were subjected to dissolution tests in phosphate buffer (USP XXIII) for a period of 24 hours maintaining a pH value of 6.4 for the first hour and 7.4 for the remaining 23 hours.

Figure 3:
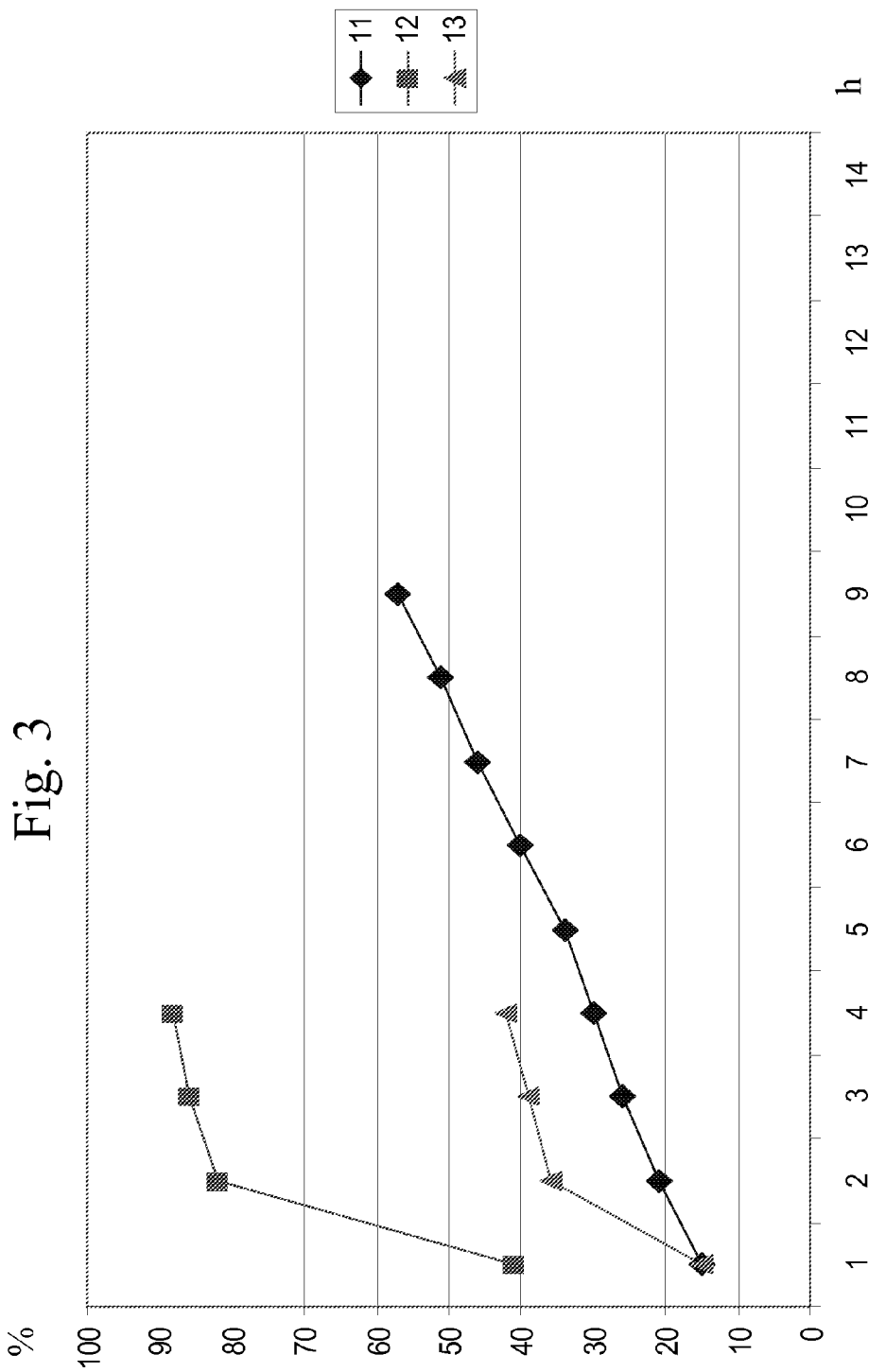
FIG. 3 shows the release profile for tablets 11 and 12 in Example 4.

The results are illustrated in Table R3 below and in FIG. 3.

TABLE R3

|  | 11 ($^I$) | 12 ($^C$) | 13 ($^C$) |
|---|---|---|---|
| Time (hours) |  | % of drug released |  |
| 1 | 16 | 41 | 31 |
| 2 | 31 | 82 | 59 |
| 3 | 40 | 86 | 71 |
| 4 | 44 | 88 | 79 |
| 5 | 49 |  | 84 |
| 6 | 56 |  | 88 |
| 7 | 65 |  | 91 |
| 8 | 76 |  | 93 |
| 9 | 94 |  | 95 |
| 10 | 97 |  | 97 |
| 11 | 100 |  | 98 |
| 12 |  |  | 100 |

($^C$): Comparison
($^I$): Invention

The data in Table R3 clearly demonstrate that tablets 12 and 13 comprising mixtures of amylopectin/starch with alginate showed no slow-release properties even if prepared in accordance with procedure C. Conversely, tablet 11 comprising the association glycogen-calcium chloride-alginate according to the present invention again showed slow-release properties with kinetics of virtually zero order over a period of approximately 9 hours.

Example 5

Preparation of Tablets 14-21

A series of tablets from 14 to 20 containing the ingredients in Table 4 were prepared in accordance with procedure C. The active ingredient used was trazodone hydrochloride.

TABLE 4

|  | 14($^I$) | 15($^I$) | 16($^I$) | 17($^I$) | 18($^I$) | 19($^I$) | 20($^I$) | 21($^I$) |
|---|---|---|---|---|---|---|---|---|
| Polymer | Polglumyt/ Alginate | Polglumyt/ AlginateM | Polglumyt/ Alginate | Polglumyt/ Alginate | Polglumyt/ Alginate | Polglumyt/ Alginate | Polglumyt/ Alginate | Polglumyt/ Alginate |
| Ratio | 70/30 | 70/30 | 60/40 | 80/20 | 60/40 | 50/50 | 80/20 | 80/20 |
| 0.1 N CaCl$_2$ solution (ml/100 ml) | 7 | 9 | 12 | 12 | 12 | 15 | 6 (BaCl$_2$) | 6 (SrCl$_2$) |
| % polymer in solution (W/V) | 2 | 2 | 2 | 8 | 2 | 2 | 2 | 2 |
| % active ingredient (W/W) | 23 | 23 | 23 | 40 | 40 | 23 | 23 | 23 |

($^I$)Invention
Polglumyt: glycogen comprising less than 60 ppm of nitrogen and less than 0.25% by weight of reducing sugars prepared in accordance with the procedure described in EP 654,048.
Alginate: sodium alginate from brown algae, viscosity of the 2% solution at 25° C. approximately 250 cPs. Manufacturer Sigma-Aldrich. Manufacturer's code SIGMA A2158.
AlginateM: sodium alginate from brown algae, viscosity of the 2% solution at 25° C. approximately 3500 cps. Manufacturer Sigma-Aldrich. Manufacturer's code SIGMA A2033.

Figure 4:
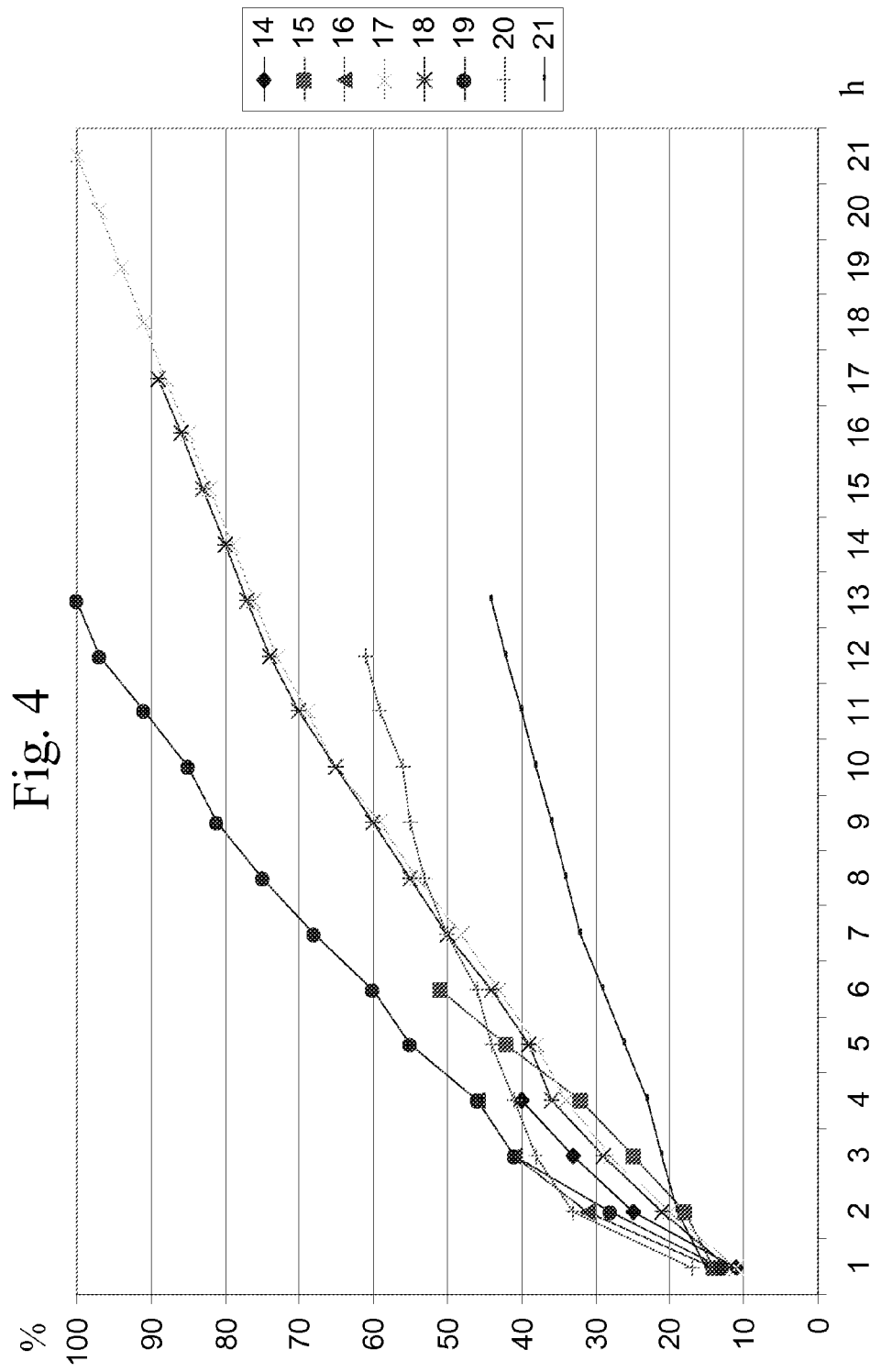
FIG. 4 shows the release profile for tablets 14 to 21 in Example 5.

Tablets 14 to 21 were subjected to dissolution tests in phosphate buffer (USP XXIII) for a period of 24 hours maintaining a pH value of 6.4 for the first hour and 7.4 for the remaining 23 hours.
The results are illustrated in Table R4 below and in FIG. 4.

TABLE R4

| Time (hours) | 14($^I$) | 15($^I$) | 16($^I$) | 17($^I$) | 18($^I$) | 19($^I$) | 20($^I$) | 21($^I$) |
|---|---|---|---|---|---|---|---|---|
|  | | | | % of drug released | | | | |
| 1 | 11 | 15 | 11 | 11 | 12 | 13 | 17 | 15 |
| 2 | 36 | 26 | 24 | 20 | 21 | 28 | 33 | 19 |
| 3 | 42 | 35 | 34 | 28 | 29 | 41 | 38 | 21 |
| 4 | 48 | 40 | 43 | 34 | 36 | 46 | 41 | 23 |
| 5 | 53 | 47 | 51 | 38 | 39 | 55 | 44 | 26 |
| 6 | 59 | 57 | 61 | 43 | 44 | 60 | 46 | 29 |
| 7 | 65 | 68 | 69 | 48 | 50 | 68 | 50 | 32 |
| 8 | 73 | 82 | 78 | 54 | 55 | 75 | 53 | 34 |
| 9 | 80 | 96 | 86 | 59 | 60 | 81 | 55 | 36 |
| 10 | 88 | 100 | 92 | 65 | 65 | 85 | 56 | 38 |
| 11 | 94 |  | 96 | 69 | 70 | 91 | 59 | 40 |
| 12 | 98 |  | 99 | 73 | 74 | 97 | 61 | 42 |
| 13 | 100 |  | 100 | 76 | 77 | 100 |  | 44 |
| 14 |  |  |  | 79 | 80 |  |  |  |
| 15 |  |  |  | 82 | 83 |  |  |  |
| 16 |  |  |  | 85 | 86 |  |  |  |

($^C$)Comparison
($^I$)Invention

The data in Table R4 clearly demonstrate that tablets 14-21 according to the present invention comprising the association of glycogen-salt-alginate according to the present invention again have slow-release properties with kinetics of almost zero order over a period which in the case of tablet 17 amounted to 21 hours.

Variations in the qualitative and quantitative ratios between the various components of the slow-release excipient according to the present invention and/or between various components of the tablets according to the present invention proved not to be critical. Conversely, tablets comprising the association glycogen-salt-alginate according to the present invention with glycogen/alginate ratios other than 80/20 (for example tablets 18 and 19) or with a different salt (tablet 20), or again with a quantity of active ingredient of more than 23% (for example tablets 17 and 18) showed slow-release properties which were identical to or superior to those of the tablets evaluated in the preceding examples.

Example 6

Preparation of Tablets 22-25

A series of tablets from 22 to 25 containing the ingredients in Table 5 were prepared using the procedure and the active ingredient indicated in Table 5.

TABLE 5

|  | 22 ($^C$) | 23 ($^C$) | 24 ($^I$) | 25 ($^I$) |
|---|---|---|---|---|
| Polymer | Polglumyt | Polglymyt/ Alginate | Polyglumyt/ Alginate | Polglumyt/ Alginate |
| Ratio | 100 | 80/20 | 80/20 | 80/20 |
| Procedure | B | B | C | C |
| 0.1 N CaCl$_2$ solution (ml/100 ml) | — | — | 12 | 12 |
| % polymer in solution (W/V) | — | — | 8 | 8 |
| % active ingredient (W/W) | 23 PCTML | 23 PCTML | 23 PCTML | 23 NPSSN |

Figure 5:
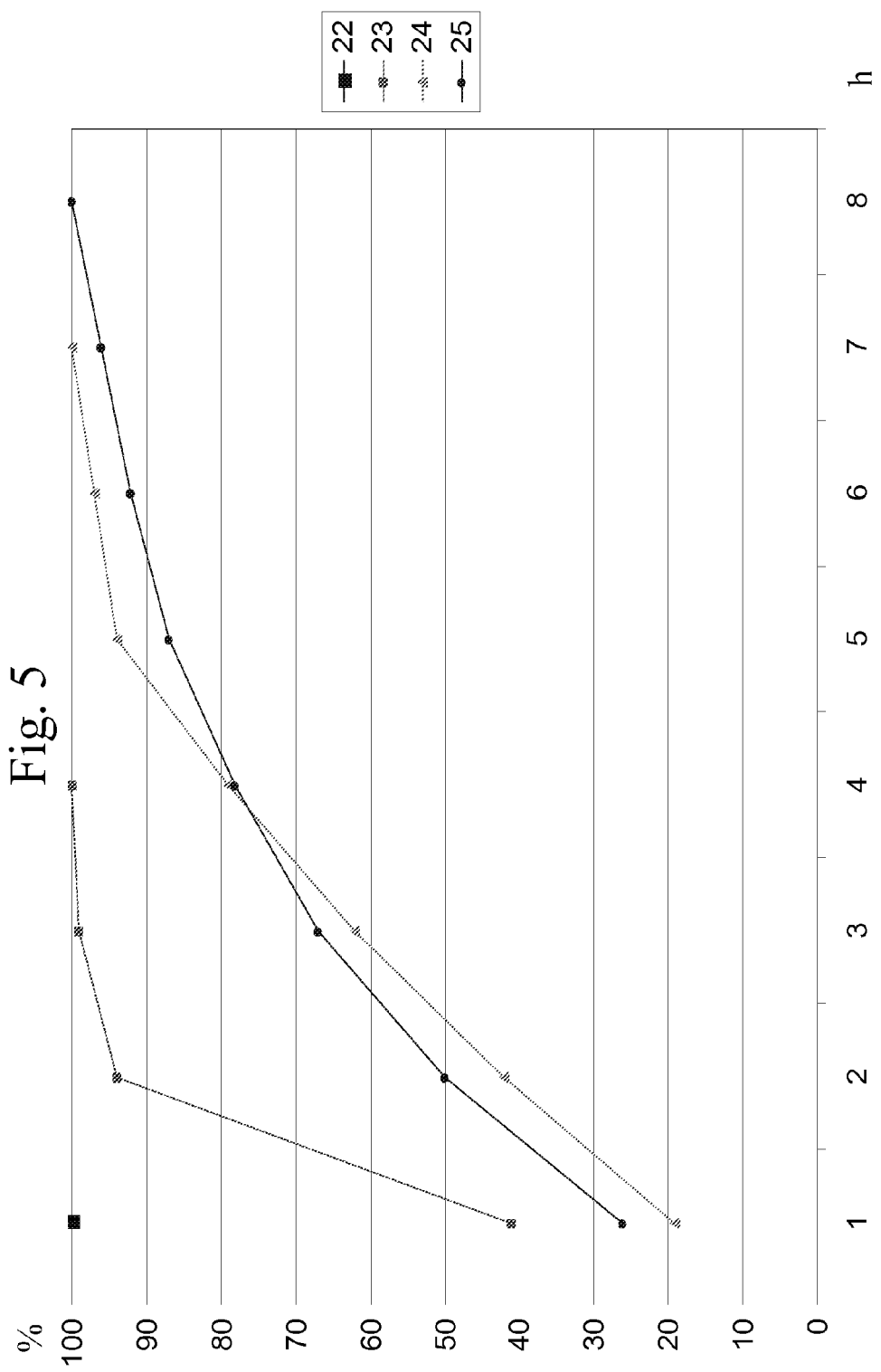
FIG. 5 shows the release profile for tablets 22 to 25 in Example 6.

($^C$): Comparison
($^I$): Invention
Polglumyt: glycogen comprising less than 60 ppm of nitrogen and less than 0.25% by weight of reducing sugars prepared in accordance with the procedure described in EP 654,048.
Alginate: sodium alginate from brown algae, viscosity of the 2% solution at 25° C. approximately 250 cPs. Manufacturer Sigma-Aldrich. Manufacturer's code SIGMA A2158.
PCTML: Paracetamol
NPSSN: Sodium Naproxen Tablets 22 to 25 were subjected to dissolution tests in phosphate buffer (USP XXIII) for a period of 24 hours maintaining a pH value of 6.4 for the first hour and 7.4 for the remaining 23 hours.
The results are illustrated in Table R5 below and in FIG. 5.

TABLE R5

| Time (hours) | 22 ($^C$) | 23 ($^C$) | 24 ($^I$) | 25 ($^I$) |
|---|---|---|---|---|
|  | | % of the drug released | | |
| 1 | 100 | 41 | 19 | 26 |
| 2 |  | 94 | 42 | 50 |
| 3 |  | 99 | 62 | 67 |
| 4 |  | 100 | 79 | 78 |
| 5 |  |  | 94 | 87 |
| 6 |  |  | 97 | 92 |
| 7 |  |  | 100 | 96 |
| 8 |  |  |  | 100 |

($^C$): Comparison
($^I$): Invention

The data in Table R5 clearly show that tablets 24 and 25 according to the present invention, comprising the association glycogen-salt-alginate according to the present invention, again showed slow-release properties with kinetics of almost zero order over a period of 7-8 hours even in the case of drugs having a very high intrinsic release rate such as paracetamol and sodium naproxen.

Example 7

Preparation of Tablets 26-27

A series of tablets from 26 to 27 containing the ingredients in Table 6 were prepared in accordance with procedure C. The active ingredient used was trazodone hydrochloride.

TABLE 6

| | 26 ($^I$) | 27 ($^I$) |
|---|---|---|
| Polymer | Glycogen O/ Alginate | Glycogen B/ Alginate |
| Ratio | 80/20 | 80/20 |
| 0.1 N CaCl$_2$ solution (ml/100 ml) | 6 | 8 |
| % polymer in solution (W/V) | 2 | 2 |
| % active ingredient (W/W) | 23 | 23 |

($^I$): Invention
Glycogen O: glycogen extracted from oysters. Manufacturer Sigma-Aldrich. Manufacturer's code SIGMA G8751, comprising 2600 ppm of nitrogen and 1027 ppm (approximately 0.1% by weight) of reducing sugars.
Glycogen B: glycogen extracted from bovine liver. Manufacturer Sigma-Aldrich. Manufacturer's code SIGMA G0885, comprising 626 ppm of nitrogen and 9373 ppm (approximately 0.9% by weight) of reducing sugars.
Alginate: sodium alginate from brown algae, viscosity of the 2% solution at 25° C. approximately 250 cPs. Manufacturer Sigma-Aldrich. Manufacturer's code SIGMA A2158.

Tablets 26 and 27 were subjected to dissolution tests in phosphate buffer (USP XXIII) for a period of 24 hours maintaining a pH value of 6.4 for the first hour and 7.4 for the remaining 23 hours.

Figure 6:
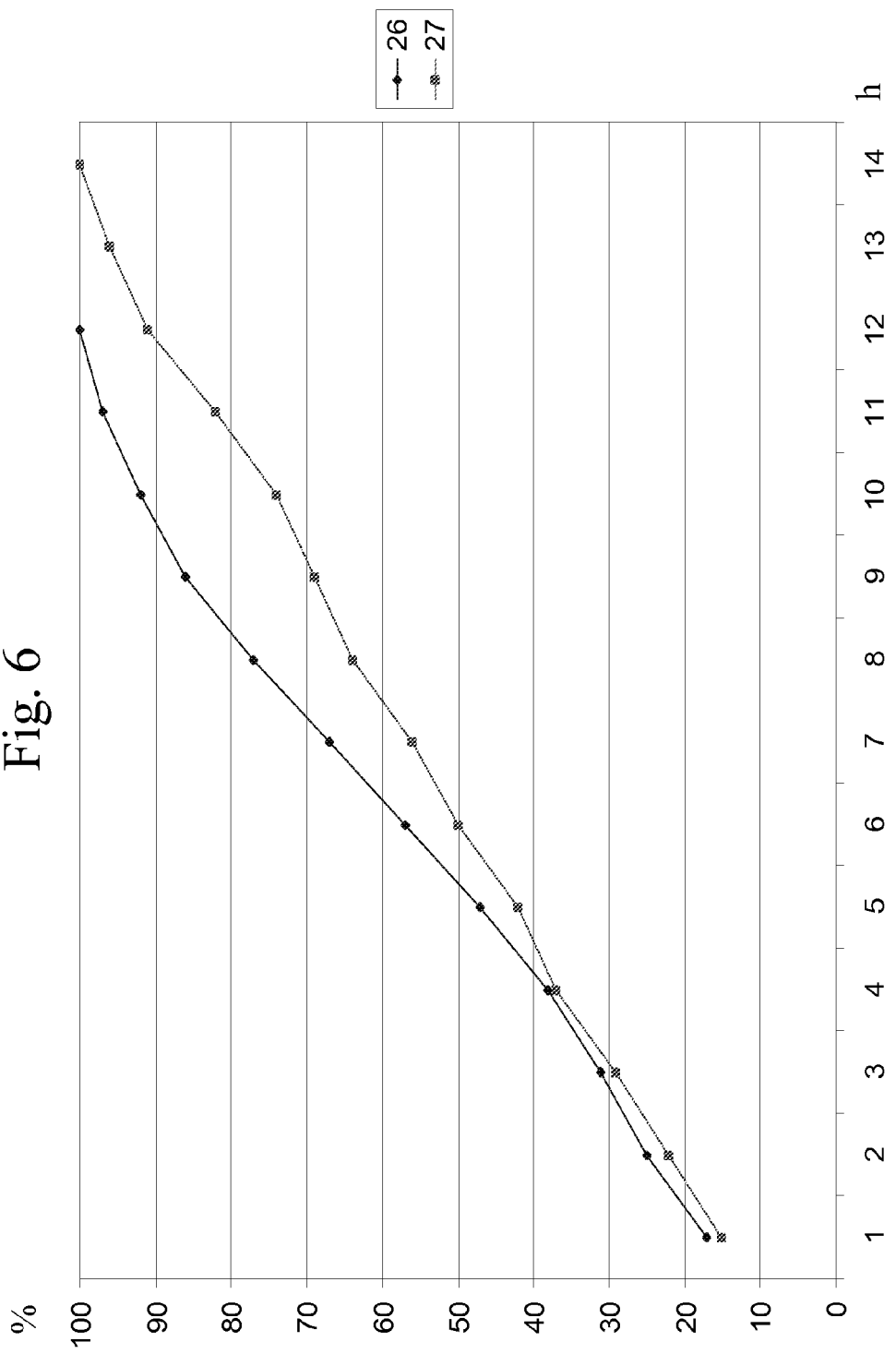
FIG. 6 shows the release profile for tablets 26 and 27 in Example 7.

The results are illustrated in Table R6 below and in FIG. 6.

TABLE R6

| | 26 ($^I$) | 27 ($^I$) |
|---|---|---|
| Time (hours) | % of drug released | |
| 1 | 17 | 15 |
| 2 | 25 | 22 |
| 3 | 31 | 29 |
| 4 | 38 | 37 |
| 5 | 47 | 42 |
| 6 | 57 | 50 |
| 7 | 67 | 56 |
| 8 | 77 | 64 |
| 9 | 86 | 69 |
| 10 | 92 | 74 |
| 11 | 97 | 82 |
| 12 | 100 | 91 |
| 13 | | 96 |
| 14 | | 100 |

($^c$): Comparison
($^I$): Invention

Example 8

Industrial Preparation 260 g of the association glycogen-calcium chloride-alginate according to the present invention were prepared in accordance with the procedure C described above using a quantity of polymer equal to 8% with a glycogen/alginate ratio of 80:20 and with 12 ml of 0.1 N CaCl$_2$ solution and charged together with 173 g of trazodone hydrochloride into a Glatt GCPG1 granulator in which the mixture was granulated with water and dried so as to reduce the moisture content to less than 5% by weight. The granulation and drying conditions are shown in Table 6 below.

TABLE 6

| Mixing | |
|---|---|
| Mixing time | 7 minutes |
| Flap aperture | 10% |
| Inlet air temperature | 65° C. |
| Wetting | |
| Wetting time | 10 minutes |
| Quantity of water | 300 g |
| Pump velocity | 10-15 rpm |
| Inlet air temperature | 65° C. |
| Granulation/drying | |
| Processing time | 10 minutes |
| Inlet air temperature | 65° C.-55° C. |
| Flap aperture | 20%-25% |
| Granulate final temperature | 45° C. |
| Final moisture content | <5% |

The granulate so obtained was discharged into a mixing drum. 2.1 g of Aerosil® (a glidant based on colloidal silica produced by Degussa Agilent GmbH, Frankfurt, Germany) were added to the granulate, mixed for approximately 2 minutes, and then the resulting mixture was sieved through a 30 Mesh sieve and then mixed for a further 5 minutes. 6.4 g of PRUV® (a lubricating agent based on sodium stearyl fumarate manufactured by JRS Pharma GmbH, Rosemberg, Germany) was added to the resulting mixture and then mixed for a further 5 minutes. The mixture so obtained was compressed in a model AMBS rotary tabletter with six stations and gravity feed.

The invention claimed is:
1. A slow-release pharmaceutical formulation, comprising: at least one active ingredient which is dispersed in a matrix, wherein said matrix comprises at least one slow-release excipient, which comprises an association of at least one glycogen and at least one alginate with an alkaline-earth metal salt
wherein said at least one active ingredient is released over a period of at least 7 hours.
2. The slow-release pharmaceutical formulation according to claim 1, wherein said at least one glycogen comprises less than 1% by weight of reducing sugars.
3. The slow-release pharmaceutical formulation according to claim 1, wherein said at least one glycogen comprises less than 0.25% by weight of reducing sugars.
4. The slow-release pharmaceutical formulation according to claim 1, wherein said at least one glycogen comprises less than 3,000 ppm of nitrogen.
5. The slow-release pharmaceutical formulation according to claim 1, wherein said at least one glycogen comprises less than 1,000 ppm of nitrogen.
6. The slow-release pharmaceutical formulation according to claim 1, wherein said at least one glycogen comprises less than 100 ppm of nitrogen.
7. The slow-release pharmaceutical formulation according to claim 1, wherein said at least one alginate exhibits a viscosity of from 50 to 1500 cPs at 25° C. when dissolved in water to form a 1% by weight aqueous solution.
8. The slow-release pharmaceutical formulation according to claim 1, wherein said at least one alginate exhibits a viscosity of from 50 to 500 cPs at 25 E 25° C. when dissolved in water to form a 1% by weight aqueous solution.
9. The slow-release pharmaceutical formulation according to claim 1, wherein said at least one glycogen and said at least one alginate, calculated as sodium alginate, are present in a weight ratio of between 90:10 and 10:90.

10. The slow-release pharmaceutical formulation according to claim 1, wherein said at least one glycogen and said at least one alginate, calculated as sodium alginate, are present in a weight ratio of between 90:10 and 30:70.

11. The slow-release pharmaceutical formulation according to claim 1, which comprises said association in an amount of between 95% by weight and 50% by weight, relative to the total weight of said pharmaceutical formulation.

12. The slow-release pharmaceutical formulation according to claim 1, wherein said alkaline-earth metal salt is a water soluble salt of a metal selected from the group consisting of magnesium, calcium, strontium, and barium.

13. The slow-release pharmaceutical formulation according to claim 1, wherein said alkaline-earth metal salt is selected from the group consisting of magnesium chloride, calcium chloride, strontium chloride, barium chloride, magnesium bromide, calcium bromide, barium bromide, strontium bromide, barium iodide, calcium iodide, strontium iodide, magnesium sulfate, magnesium carbonate, calcium bicarbonate, magnesium bicarbonate, barium bicarbonate, and calcium dihydrogen phosphate.

14. The slow-release pharmaceutical formulation according to claim 1, wherein said alkaline-earth metal salt is selected from the group consisting of calcium chloride, calcium bromide, barium chloride, barium bromide, strontium chloride, and strontium bromide.

15. The slow-release pharmaceutical formulation according to claim 1, wherein said association comprises said alkaline-earth metal salt in an amount of between 0.050 and 5.000 millimoles per gram of glycogen/alginate mixture.

16. The slow-release pharmaceutical formulation according to claim 1, wherein said association comprises said alkaline-earth metal salt in an amount of between 0.100 and 2.000 millimoles per gram of glycogen/alginate mixture.

17. The slow-release pharmaceutical formulation according to claim 1, wherein said association comprises said alkaline-earth metal salt in an amount of between 0.100 and 1.000 millimoles per gram of glycogen/alginate mixture.

18. The slow-release pharmaceutical formulation according to claim 1, wherein said at least one active ingredient is at least one selected from the group consisting of an analgesic, an antipyretic, an antibiotic, an antihistamine, an anxiolytic, an anti-inflammatory, an antacid, a vasodilator, a vasoconstrictor, a stimulant, a decongestant, an anticoagulant, an antiarrhythmic, a hypoglycaemic agent, a diuretic, an antidepressant, an antiasthmatic, an anti-emetic, and an antihypotensive and an antispasmodic agent.

19. The slow-release pharmaceutical formulation according to claim 1, wherein said at least one active ingredient is at least one selected from the group consisting of ibuprofen, paracetamol, prulifloxacin, levocetirizine dihydrochloride, lorazepam, naproxen, ranitidine hydrochloride, isosorbide, naphazoline nitrate, pyracetam, ticlopidine hydrochloride, propaphenone hydrochloride, glimepiride, furosemide, trazodone hydrochloride, flunisolide, and dimehydrinate.

20. The slow-release pharmaceutical formulation according to claim 1, wherein said at least one active ingredient is present in an amount of between 5% by weight and 50% by weight, relative to the total weight of said pharmaceutical formulation.

21. The slow-release pharmaceutical formulation according to claim 1, wherein said at least one slow-release excipient is at least one selected from the group consisting of an antiadherence agent, a binder, a disintegrator, a filler, a diluent, a flavoring, a coloring agent, a fluidizer, a lubricant, a preservative, a humectant, an absorbent, and a sweetener.

22. The slow-release pharmaceutical formulation according to claim 1, which is a suspension, an emulsion, a powder, a tablet, a granulate, a pellet, a capsule, a lozenge, or a pill.

23. The slow-release pharmaceutical formulation according to claim 22, further comprising an enteric coating.

24. An excipient, comprising an association of at least one glycogen and at least one alginate with an alkaline-earth metal salt, wherein said at least one glycogen comprises less than 1% by weight of reducing sugars.

25. A process for the production of a slow-release excipient, which comprises an association of at least one glycogen and at least one-alginate with an alkaline-earth metal salt, said process comprising:
    (a) dissolving said at least one glycogen and said at least one alginate in a hydrophilic medium;
    (b) adding a salt of a soluble alkaline-earth metal to the hydrophilic medium;
    (c) stirring said hydrophilic medium and allowing it to stand until said hydrophilic medium forms a hydrogel; and
    (d) dehydrating said hydrogel,
    wherein said slow-release excipient permits the release of at least one active ingredient over a period of at least 7 hours.

26. The process according to claim 25, wherein said hydrophilic medium is selected from the group consisting of distilled water, demineralized water, and deionized water.

27. The process according to claim 25, wherein said at least one glycogen and said at least one alginate, calculated as sodium alginate, are dissolved in said hydrophilic medium in a total amount of between 1% by weight and 20% by weight relative to the volume of the hydrophilic medium.

28. The process according to claim 25, wherein said at least one glycogen and said at least one alginate, calculated as sodium alginate, are dissolved in said hydrophilic medium in a total amount of between 1% and 15% by weight relative to the volume of the hydrophilic medium.

29. The process according to claim 25, wherein said at least one glycogen and said at least one-alginate, calculated as sodium alginate, are dissolved in said hydrophilic medium in a weight ratio of between 90:10 and 10:90.

30. The process according to claim 25, wherein said alkaline-earth salt is added to said hydrophilic medium in an amount of between 0.050 and 5.000 millimoles per gram of said at least one glycogen and said at least one alginate.

31. The process according to claim 25, wherein said stirring in (c) is maintained for a period of between 10 and 120 minutes.

32. The process according to claim 25, wherein said hydrophilic medium is allowed to stand for a period of between 6 and 24 hours.

33. A process for the production of a slow-release pharmaceutical formulation, which comprises at least one active ingredient dispersed in a matrix, which comprises at least one slow-release excipient, said process comprising:
    (1) preparing said at least one slow-release excipient by a process according to claim 25:
    (2) mixing said at least one active ingredient with said slow-release excipient:
    (3) optionally, adding at least one further excipient: and
    (4) producing a pharmaceutical formulation selected from the group consisting of a suspension, an emulsion, a powder, a tablet, a granulate, a pellet, a capsule, a lozenge, or a pill,
    wherein the at least one active ingredient is released from said slow-release formulation over a period of at least 7 hours.

34. A process for manufacturing a slow-release pharmaceutical formulation, comprising adding an excipient produced by a process according to claim 25 to a pharmaceutical formulation.

35. The slow-release pharmaceutical formulation of claim 1, wherein said at least one active ingredient is released over a period of at least 12 hours.

36. The slow-release pharmaceutical formulation of claim 1, wherein the release kinetics of said at least one active ingredient are substantially of zero order.

37. The slow-release pharmaceutical formulation of claim 1, wherein the release of said at least one active ingredient is constant over time.

* * * * *